United States Patent
Biewer et al.

(10) Patent No.: US 11,013,840 B2
(45) Date of Patent: May 25, 2021

(54) SMART CART FOR A DIALYSIS MACHINE

(71) Applicant: Fresenius Medical Care Holdings, Inc., Waltham, MA (US)

(72) Inventors: John Aaron Biewer, Waltham, MA (US); Kulwinder S. Plahey, Martinez, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 244 days.

(21) Appl. No.: 16/008,092

(22) Filed: Jun. 14, 2018

(65) Prior Publication Data
US 2019/0381229 A1    Dec. 19, 2019

(51) Int. Cl.
| | |
|---|---|
| *A61M 1/16* | (2006.01) |
| *A61B 50/13* | (2016.01) |
| *A61M 1/28* | (2006.01) |
| *A61B 5/00* | (2006.01) |
| *B62B 3/10* | (2006.01) |

(52) U.S. Cl.
CPC ............ *A61M 1/1603* (2014.02); *A61B 5/742* (2013.01); *A61B 50/13* (2016.02); *A61M 1/28* (2013.01); *B62B 3/106* (2013.01); *A61M 2209/084* (2013.01)

(58) Field of Classification Search
CPC .............. A61M 1/1601; A61M 1/1603; A61M 2209/084; A61B 50/13
See application file for complete search history.

(56) References Cited

U.S. PATENT DOCUMENTS

| | | | |
|---|---|---|---|
| 9,186,449 B2 | 11/2015 | Singh et al. | |
| 2013/0106609 A1* | 5/2013 | Singh | A61M 1/288 340/573.1 |
| 2015/0227127 A1* | 8/2015 | Miller | G16H 20/13 700/244 |
| 2016/0074565 A1* | 3/2016 | Giordano | A61M 1/1654 210/85 |
| 2018/0289879 A1* | 10/2018 | Fulkerson | A61M 1/267 |

* cited by examiner

*Primary Examiner* — Jason E Flick
*Assistant Examiner* — Tasnim Mehjabin Ahmed
(74) *Attorney, Agent, or Firm* — Muirhead and Saturnelli, LLC

(57) ABSTRACT

An intelligent support assembly, for example, a mobile support assembly (e.g., cart) for a dialysis machine (e.g., a peritoneal dialysis cycler), and methods for performing dialysis treatment using such an assembly. The intelligent support assembly may be configured to determine one or more properties relating to a dialysis treatment being performed on a patient using the dialysis machine, and to control one or more actions that affect the dialysis treatment based at least in part on the determined one or more properties. The cart may be configured to receive information corresponding to the one or more properties from, and transmit such information to, the dialysis machine, network access devices, sensor devices, and other devices. The controlled actions may include adjusting a height of dialysis solution or other items relative to a height of the patient, and moving the cart relative to the location of the patient.

18 Claims, 2 Drawing Sheets

SMART CART FOR A DIALYSIS MACHINE

TECHNICAL FIELD

This application generally relates to dialysis machines and, in particular, an intelligent cart for use with dialysis machines.

DESCRIPTION OF RELATED ART

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many automated PDs (e.g., "cyclers") are designed to automatically infuse, dwell, and drain dialysate to and from the patient's peritoneal cavity. The treatment typically lasts for several hours, often beginning with an initial drain procedure to empty the peritoneal cavity of used or spent dialysate. The sequence then proceeds through the succession of fill, dwell, and drain phases that follow one after the other. Each phase is called a cycle.

Automated dialysis machines (ADMs), including automated PD and HD machines, are often supported on a mobile support assembly, e.g., a cart. This allows the ADM to be moved with less manual effort than if carried, for example, in a hospital, clinic or in-home use. For example, the cart allows the ADM to be moved along with a patient, or between the patient and wherever the ADM is kept or maintained when not in use. A cart that is used to support and move an ADM may be referred to herein as an ADM cart.

Currently, ADM carts do not provide much more than basic cart functionality. It is desirable to have an ADM cart that can do more.

SUMMARY OF THE INVENTION

According to some embodiments the system described herein, a support assembly for a dialysis machine is provided. The support assembly includes one or more substantially planar platforms, at least a first of the one or more substantially planar platforms supporting the dialysis machine. The support assembly also includes a control unit that determines one or more properties relating to a dialysis treatment being performed on a patient using the dialysis machine, communicates information relating to the one or more properties to the dialysis machine, and controls one or more actions that affect the dialysis treatment based at least in part on the one or more properties. The control unit may include platform control logic that controls a height of the first platform based on at least one of the one or more properties, and the at least one property may include: a height of the dialysis machine and a height of the patient. The support assembly may include a display screen that displays information associated with the dialysis treatment, one or more support members for supporting a bag of solution coupled to the dialysis machine that supplies the solution introduced into the patient during the dialysis treatment, and a liquid fill-level sensor that detects a height of solution in the bag as the solution is emptied from the bag into the patient during the dialysis treatment, where the height of the solution is one of the one or more properties and wherein the one or more actions include adjusting the height of the bag based on the height of the fluid in the bag to attempt to maintain a constant height of the fluid relative to an entry point of the solution into the patient during the dialysis treatment. The control unit may include a memory storing parameter values corresponding to one or more types of dialysis machines, where the support assembly includes a dialysis machine sensor that detects a type of the dialysis machine, wherein the one or more properties includes the detected type of the dialysis machine, wherein the control unit controls the one or more actions based at least in part on the detected type of the dialysis machine. The support assembly may include a user interface that receives manual input from a user, where the control unit controls the one or more actions based at least in part on the manual input from the user, and may include three or more wheels that provide horizontal movement of the support assembly and a powered motor coupled to at least one of the at least three wheels to provide powered movement of the cart. At least one of the properties may indicate a location of the patient, and the support assembly may further include a steering control unit coupled to at least one of the three wheels that controls the at least one wheel to turn laterally, and a position control unit coupled to the steering control mechanism and the powered motor that receives the at least one property indicating the location of the patient, detects a change in location of the patient, and controls the steering control unit and the powered motor to cause movement of the support assembly in response to the detected change.

In some embodiments of the system described herein, a method of providing dialysis treatment on a patient may be performed. The method a support assembly for a dialysis machine determining one or more properties relating to the dialysis treatment being performed using the dialysis machine, the support assembly communicating information relating to the one or more properties to the dialysis machine, and the support assembly controlling one or more actions that affect the dialysis treatment based at least in part on the one or more properties. Controlling one or more actions may include controlling a height of the first platform based on at least one of the one or more properties, and the at least one property may include a height of the dialysis machine and a height of the patient. The support assembly may include a display screen, and the method further include displaying information associated with the dialysis treatment on the display screen. The support assembly may include one or more support members for supporting a bag of solution coupled to the dialysis machine that supplies the solution introduced into the patient during the dialysis treatment, determining one or more properties may include detecting a height of solution in the bag as the solution is emptied from the bag into the patient during the dialysis treatment, and controlling the one or more actions may includes adjusting the height of the bag based on the height of the fluid in the bag to attempt to maintain a constant height of the fluid relative to an entry point of the solution into the patient during the dialysis treatment. The support assembly may include a memory storing parameter values corresponding to one or more types of dialysis machines, where determining one or more properties includes detecting a type of the dialysis machine, and where the one or more actions are controlled based at least in part on the detected type of the dialysis machine. The support assembly may include a user interface, where the method further includes receiving manual input from a user through the user interface, and where the one or more actions are controlled based at least in part on the manual input from the user. The support assembly may include three or more wheels that provide horizontal movement of the support assembly, and a powered motor coupled to at least one of the at least three wheels to provide powered movement of the cart, where the method includes controlling the motor to control movement of the cart. The support assembly may include a steering control unit coupled to at least one of the three wheels that controls the at least one wheel to turn laterally, where determining one or more properties includes determining a location of the patient and detecting a change in location of the patient, and where controlling one or more actions includes controlling the steering control unit and the powered motor to cause movement of the support assembly in response to the detected change.

In some embodiments of the system described herein, a non-transitory computer-readable medium having software stored thereon for providing dialysis treatment on a patient using a support assembly on which a dialysis machine is supported is provided. The software includes executable code uses the support assembly to determine one or more properties relating to the dialysis treatment being performed using the dialysis machine, executable code that communicates information relating to the one or more properties from the support assembly to the dialysis machine, and executable code that uses the support assembly to control one or more actions that affect the dialysis treatment based at least in part on the one or more properties. The support assembly may include one or more support members for supporting a bag of solution coupled to the dialysis machine that supplies the solution introduced into the patient during the dialysis treatment, and a liquid fill-level sensor that detects a height of solution in the bag as the solution is emptied from the bag into the patient during the dialysis treatment, where the software further includes executable code that controls adjusting the height of the bag based on the height of the fluid in the bag to attempt to maintain a constant height of the fluid relative to an entry point of the solution into the patient during the dialysis treatment. The executable code that controls one or more action may include executable code that controls a height of the first platform based on at least one of the one or more properties. The at least one property may include a height of the dialysis machine and a height of the patient. The support assembly may include a display screen, where the software includes executable code that controls displaying information associated with the dialysis treatment on the display screen. The support assembly may include a memory storing parameter values corresponding to one or more types of dialysis machines, where the executable code that determines one or more properties includes the executable code that detects a type of the dialysis machine, and where the executable code that controls the one or more actions controls the one or more actions based at least in part on the detected type of the dialysis machine. The support assembly may include a user interface, where the software further includes the executable code that receives manual input from a user through the user interface, and the executable code that controls one or more actions controls the one or more based at least in part on the manual input from the user. The support assembly may include three or more wheels that provide horizontal movement of the support assembly, and a powered motor coupled to at least one of the at least three wheels to provide powered movement of the cart, wherein the software includes the executable code that controls the motor to control movement of the cart. The support assembly may include a steering control unit coupled to at least one of the three wheels that controls the at least one wheel to turn laterally, where the executable code that determines one or more properties includes executable code that determines a location of the patient and detects a change in location of the patient, and where the executable code that controls one or more actions includes executable code to control the steering control unit and the powered motor to cause movement of the support assembly in response to the detected change.

BRIEF DESCRIPTION OF THE DRAWINGS

Features and advantages of the system described herein will become more apparent from the following detailed description of illustrative embodiments thereof taken in conjunction with the accompanying drawings in which.

DETAILED DESCRIPTION OF EMBODIMENTS

Today's ADM carts may have some automated capabilities. For example, U.S. Pat. No. 9,186,449 to Singh et al., entitled "Dialysis Machine Support Assemblies and Related Systems and Methods", the entire contents of which are herein incorporated by reference, describes an ADM cart that can receive sensor input data from an ADM and adjust the vertical position of one of its platform on which the ADM is disposed based on the sensor input data. The system described herein presents an ADM cart that can provide additional automation to assist in dialysis treatment to a patient.

Described herein is an intelligent support assembly, for example, a mobile support assembly (e.g., cart) for an ADM (e.g., a PD cycler), and methods for performing dialysis treatment using such an assembly. It should be appreciated that the ADM may be a gravity-feed or pump-based ADM. Some embodiments of the system described herein, including embodiments of such an assembly and/or methods, will be described using the illustrative example of a cart, but it should be appreciated that the system described herein is not so limited, as other types of support assemblies, including non-mobile support assemblies, are possible, and intended to fall within the scope of the system described herein. For example, the term "smart cart" is used herein to refer to an intelligent support assembly according to embodiments of the system described herein, but such a smart cart need not be mobile. Further, while some embodiments of the system described herein are described primarily in relation to ADMs, it should be appreciated that the system described herein is not so limited, but rather may be implemented using other types of medical devices, which are intended to fall within the scope of the system described herein.

The smart cart may be configured to determine one or more properties relating to a dialysis treatment being performed on a patient using an ADM, and to control one or more actions that affect the dialysis treatment based at least in part on the determined one or more properties. The cart may be configured to receive information corresponding to the one or more properties from, and transmit such information to, the ADM, sensor devices, remote entities (e.g., via network access devices (i.e., gateways)); other devices, or any suitable combination of the foregoing.

Illustrative embodiments of the invention will now be described in more detail in relations to the figures.

Figure 1:
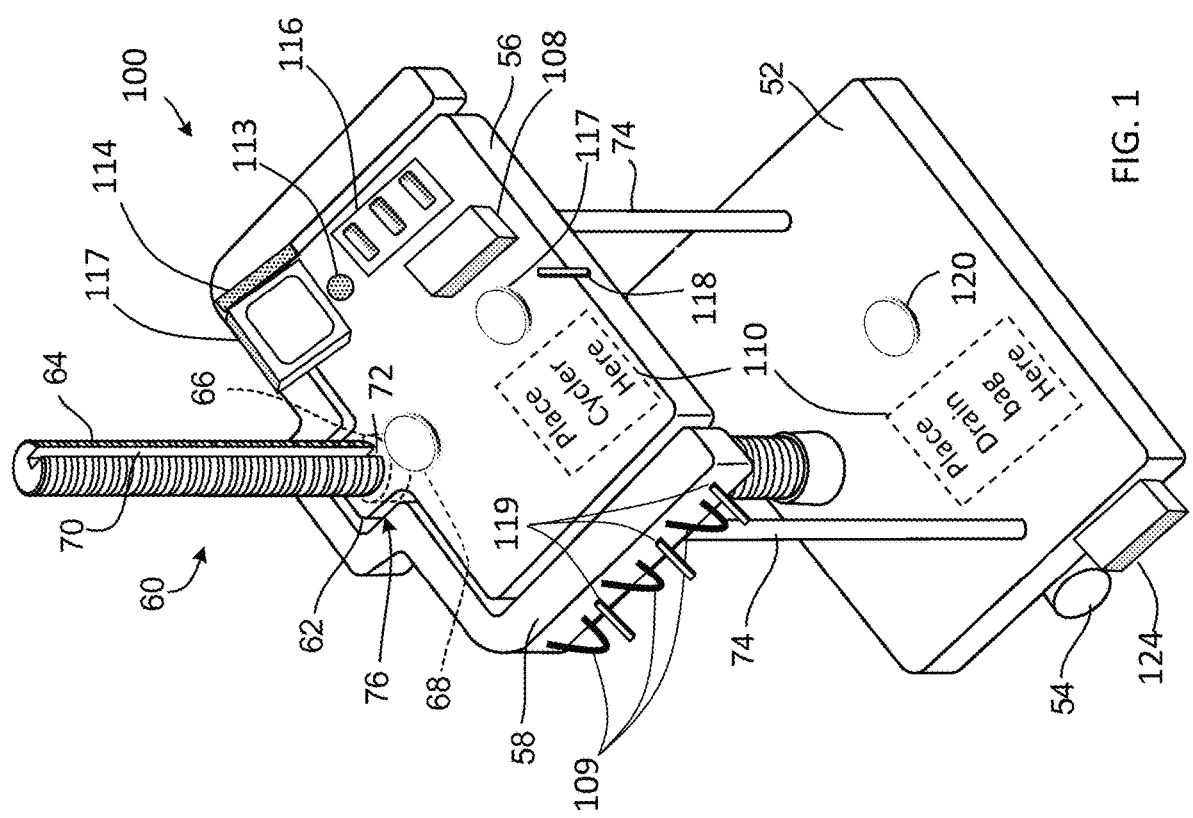
FIG. 1 is a block diagram illustrating an example of a smart cart for an automated dialysis machine, according to embodiments of the system described herein.

FIG. 1 is a block diagram illustrating an example of a smart cart 100 for an ADM 100, according to embodiments of the system described herein. Other embodiments of a mobile support assembly, for example, variations of smart cart 100, are possible and are intended to fall within the scope of the system described herein.

The smart cart 100 may include any of: a base 52, one or more stationary platforms 58, one or more vertically moveable platforms 56; leg members 74; solution bag supports 109; three or more wheels 54; a control unit 108; one or more instruction areas 110; a display unit 112; a microphone 113; one or more speakers 114; a tactile user interface 116; an ADM sensor 117; an ADM treatment set sensor (i.e., a "set sensor") 118; one or more drain bag sensors 120; a platform drive unit 60; a wheel drive unit 124; other components; or any suitable combination of the foregoing.

The base 52 may be a substantially flat, planar member that is mounted on top of the wheels 54 and provide a mounting location for the other components of the cart 100, as described in more detail herein. In some embodiments, the base 52 may be about 8 inches to about 24 inches (e.g., about 8 inches to 11 inches) wide by 6 inches to about 20 inches (e.g., 7 inches to 10 inches) deep and can be formed (e.g., molded, machined, and/or cast) of any of various suitable materials (e.g., plastics, metals, and/or composites). The base 52 may be designed to sufficiently support the other components of the cart 100. For example, the base can be made to support typically about 25 lbs. to about 100 lbs.

The wheels 54 are fastened to the bottom of the base 52 so that the cart 100 can be moved smoothly along typical floor surfaces. The wheels 54 are typically casters (e.g., rigid or swivel casters) that can be made of any of various suitable materials (e.g., plastics, metals, and/or composites).

The vertically moveable platform 56 may be a substantially flat planar member, similar to the base 52, that provides a seating location for the ADM. The vertically moveable platform 56 is typically about 8 inches to about 24 inches (e.g., about 8 inches to 11 inches) wide by 6 inches to about 20 inches (e.g., 7 inches to 10 inches) deep and can be formed (e.g., molded, machined, and/or cast) of any of various suitable materials (e.g., plastics, metals, and/or composites). The vertically moveable platform 56 may be designed to sufficiently support the weight of the ADM while stationary, as well as when articulating up and down. For example, the vertically moveable platform can be made to support typically about 35 lbs. to about 122 lbs. During dialysis treatments, the vertically moveable platform 56 may be moved up and down via the platform drive unit 60, as described in more detail elsewhere herein. The vertically moveable platform 56 also may include an extension 62 that contains certain components of the platform drive unit 60, as described in more detail elsewhere herein.

The platform drive unit 60 may be used to move the vertically moveable platform 56 and any components disposed thereon, e.g., the ADM, up and down in a controlled and monitored manner during dialysis treatments. The platform drive unit 60 may be configured to move the vertically moveable platform 56 over a height range that is typically greater than 24 inches (e.g., about 24 inches to about 48 inches). The platform drive unit 60 includes a leadscrew 64 and a leadscrew nut 66 that may be rotated and controlled by a motor 68 during articulation. The leadscrew 64 may be mounted to the base 52 in a fixed position and extends upward from the base 52. The motor 68 and leadscrew nut 66 may be contained in the vertically moveable platform 56. As shown, the leadscrew nut 66 may be positioned in the extension 62 of the vertically moveable platform 56 so that the leadscrew nut 66 can engage the leadscrew 64. The leadscrew nut 66 may be coupled to the extension 62 such that the leadscrew nut 66 is able to rotate about its central axis with respect to the vertically moveable platform 56 and the extension 62 (e.g., via bearings that connect the leadscrew nut 66 to vertically moveable platform 56), but the leadscrew nut 66 is constrained from moving in a vertical direction with respect to the vertically moveable platform 56 and the extension 62. Therefore, as the electric motor 68 rotates the leadscrew nut 66, the leadscrew nut 66 rotates about the stationary leadscrew 64 and therefore travels upward or downward along threads of the leadscrew 64 depending on the direction of rotation of the leadscrew nut 66.

The platform drive unit 60 may include an alignment mechanism that prevents the vertically moveable platform 56 from rotating around the leadscrew 64 as the leadscrew nut 66 rotates. Although the leadscrew nut 66 is typically able to rotate freely within the extension 62 of the vertically moveable platform 56, frictional and/or inertial forces caused by the rotating leadscrew nut 66 could potentially cause the vertically moveable platform 56 to also rotate about the leadscrew 64. To prevent rotation of the vertically moveable platform 56, the leadscrew 64 may include a recessed channel 70 within the leadscrew threads that extends uniformly along the longitudinal direction of the leadscrew 64. To engage the recessed channel 70, the vertically moveable platform 56 may include a tab feature 72 that is sized to fit within the recessed channel 70. As the leadscrew nut 66 rotates around the stationary leadscrew 64 and articulates upward or downward, the tab 72 moves vertically within the recessed channel 70 and prevents the vertically moveable platform 56 from rotating. In some embodiments, the tab 72 may include linear bushings or bearings to provide smooth translation along the recess 70.

The motor 68 may be an electric motor (e.g., an electric stepper motor, other types of DC motors, or an AC motor) that is mechanically connected to the leadscrew nut 66 using gears to provide rotation to the leadscrew nut 66. The motor 68 includes electrical connections (e.g., wiring and/or a wire harness) to electrically connect the motor 68 to the ADM, which may by itself, or in conjunction with the smart cart 100, control the motion as well as monitor the position of the vertically moveable platform 56. During use, the ADM can monitor the position of the vertically moveable platform 56 by monitoring the rotation of the motor 68. By knowing an initial position (e.g., a home position) of the vertically moveable platform 56, the smart cart 100 (e.g., the control unit 108) and/or ADM 100 can count the number of stepper motor rotations or steps in order to calculate the upward or downward travel and therefore the position of the vertically moveable platform 56. By monitoring the number of motor steps, the distance of upward or downward travel of the vertically moveable platform 56 can be determined using the pitch of the leadscrew threads. To calibrate the smart cart 100 and the ADM, the initial position (e.g., the height during assembly or installation) of the vertically moveable platform 56 and the distance that the vertically moveable platform 56 travels during each motor step can be coded into software of the ADM and/or the smart cart 100 (e.g., the control unit 108). The initial position and the distance travelled per step can then be used to determine current position at a given time during operation of the smart cart 100 by counting the number of motor steps. In some implementations, other calibration techniques are possible.

It should be appreciated that the platform drive mechanism 60 described herein is just one example of a drive mechanism by which a smart cart platform can be moved vertically up and down. Any of a variety of other drive mechanisms, for example, using electro-mechanical, electro-magnetic, pneumatic or hydraulic power, or a suitable combination thereof, including variations of drive mechanism 60, are possible, and are intended to fall within the scope of the system described herein.

The stationary platform 58 may be a substantially rigid planar member mounted to the base 52 using leg members 74. Like the vertically moveable platform 56, the stationary platform 58 may be formed (e.g., molded, machined, and/or cast) of any of various suitable materials (e.g., plastics, metals, and/or composites). The stationary platform 58 may be mounted to the base 52 using the leg members 74 so that the stationary platform 58 is at a height that corresponds with a typical height of a patient during typical dialysis treatments. For example, the stationary platform can be positioned about 25 inches to about 30 inches (e.g., about 27 inches) above the ground surface. The leg members 74 may be elongated beams that can be formed of any of various suitable materials (e.g., beams, tubing, and/or other members). The leg members 74 may have sufficient column strength to support the weight of the stationary platform 58 along with any equipment that is typically disposed on the stationary platform 58. For example, the leg members may be designed to support typically about 30 lbs. to about 50 lbs. As shown in FIG. 1, the stationary platform 58 may be generally u-shaped and include an opening 76 that is sized so that the vertically moveable platform 56 and the extension 62 are not obstructed while they move up and down along the leadscrew 64. In embodiments in which the stationary platform 58 is u-shaped, fluid lines that extend from the front of the ADM typically will not get hung up during use. Other shapes of the stationary platform, for example, generally rectangular, are possible and intended to fall within the scope of the system described herein.

While only one vertically moveable platform 56 is illustrated in FIG. 1, it should be appreciated that the system described herein is not so limited, as additional vertically moveable platforms and corresponding drive units may be included in smart cart 100, and are intended to fall within the scope of the system described herein. Two or more such vertically moveable platforms may be configured/aligned so as not to overlap horizontally, so that each can be adjusted vertically to be higher or lower than, or the same height as, the other, and one or more vertically moveable platforms may be configured/aligned so that they overlap horizontally so that one always remains higher or lower than the other. Further, in some embodiments, one or more components disposed on the base 52, on a vertical platform (e.g., the vertical platform 56) or a stationary platform (e.g., the platform 58) may be configured for powered controlled movement, vertically or otherwise, independent of the level of the respective base or platform on which it is disposed. For example, the display unit 112, solution bag supports 109 and/or other components may be configured to be raised or lowered manually (e.g., using a GUI displayed on the display unit 112 or the tactile user interface 116) or in an automated fashion based on detected properties, as described in more detail elsewhere herein. To this end, each such vertically adjusted component may be configured with a drive unit (e.g., a variation of the drive unit 60) to implement the vertical movement, for example, using any of: motors, cams, gears, screws, nuts and other electronic, electro-mechanical, electro-magnetic, pneumatic or hydraulic components, other components or any suitable combination of the foregoing.

The wheel drive unit 124 may enable controlled powered lateral movement of the cart 100 via control of the wheels. The drive unit may include a wheel motor, a steering mechanism to control at least one of the wheels 54 to turn laterally, and any of a variety of other electronic, electro-mechanical, electro-magnetic, pneumatic or hydraulic components, including but not limited to cams, gears, etc. to enable the controlled powered movement of the smart cart 100. The movement may be controlled via commands received from: the tactile user interface 116; a remote-control unit, e.g., a hand-held unit of a patient; and/or an input device (e.g., keyboard, mouse, or the microphone 113 via a GUI provided on the display unit 112). Further, the drive unit 124 and/or the control unit 108 may include a position control unit that is electrically, mechanically, magnetically, pneumatically and/or hydraulically coupled to the steering control mechanism and the powered motor, which may be configured to receive information about the location of the patient, detect a change in location of the patient, and control the steering control unit and the powered motor to cause movement of the smart cart 100 in response to the detected change. For example, the position control unit may be configured to receive information from an RFID tag or the like attached to the patient, for example, an item of clothing of the patient, or the entry point of a patient line, and determine a distance and direction of the patient from the smart cart 100 from properties of the signal detected from the RFID tag using known techniques. To determine direction, multiple transmitters may be included at different locations on the cart, and the direction and distance of the user determined using known triangulation techniques. The position control unit then may electronically control the powered motor and steering mechanism of the wheel drive unit 124 to move the cart in accordance with the determined location of the patient; for example, to remain at a predefined distance from the patient.

The smart cart 100 also may include: an AC power conduit (not shown), which may include a power cord and an AC adapter, which may supply AC (alternating current) power to the smart cart 100 by electrically coupling the smart cart to an A/C power source (e.g., via an electrical outlet on a wall or a floor); and a DC power source (not shown) (e.g., battery), which may supply a DC (direct current) power source as an alternative power source, and in some embodiments may be rechargeable via the AC power conduit when it is connected to an AC power source. The smart cart 100 may include a plurality of electrical conduits that couple and provide DC power to one or more components of the cart described herein.

The one or more instruction areas 110 may be used to display instructions for setting up, using, troubleshooting and/or breaking down the ADM and/or the smart cart 100. These instructions could include the contents of what would typically be in a "Quick Start Guide" or contain troubleshooting information or FAQs or other useful information. While the areas 110 are illustrated as being on the platform 56 and base 52, it should be appreciated that one or more instruction areas can be located at other locations on the smart cart 100. Instructions may be printed or molded directly on the smart cart within the areas 110 or printed on another medium (e.g., a magnetized flexible plastic or polymer) and affixed temporarily or permanently to the one or more instruction areas 110. For example, one or more temporary cling labels or labels with pressure sensitive adhesive could be used to attach the labels to the areas 110.

Temporary labels have the benefit to allow updates to the instructions as the cart, ADM, treatment, etc. changes and/or as the patient gets more comfortable with use of the cart or the ADM and/or with the treatment. The one or more areas 110 each may be configured to include a protected area into which printed instructions can be inserted, which may have a visually transparent surface through which the instructions can be viewed while in the inserted position.

The display unit 112 may be configured to display information about the dialysis treatment, including messages, images, videos, text, animation, etc. The display unit 112 may be communicatively coupled to the control unit 108, through which the display unit 112 may be controlled. The information displayed may be any information relating to a particular dialysis treatment, or more general information about the patient and/or the dialysis therapy of the patient. The displayed information may be, or may be based on: information determined by the smart cart 100 itself, for example, raw data detected by any of its sensors and/or information determined based on such raw data; information communicated by an ADM coupled to the smart cart 100; information communicated remotely, for example, from a health care facility (e.g., clinic, hospital, research facility); health care provider (e.g., doctor, nurse, other healthcare professional, administrator) and/or one-line medical system (e.g., database, automated decision-making system), information entered by a user (e.g., patient, health care provider or other caretaker) locally via a GUI provided on the display unit 112, for example, via a touch screen interface of the display unit 112 or the tactile user interface 116; information from other sources; or any suitable combination of the foregoing. The term "permitted remote entities" is used herein to refer collectively to health care providers, health care facilities, on-line medical systems and other pertinent entities located remotely from, and communicatively coupled to, the smart cart in relation to providing treatment to a patient. Based on software or other logic executing at any of the information sources described above (e.g., smart cart itself, coupled ADM, remote sources), including predefined parameter values for such software or logic, some displayed information may be updated continually, while other information may be updated (e.g., periodically) or remain relatively constant throughout a treatment session or overall therapy. In some embodiments, the display unit may be configured to be controlled independently of the control unit 108, for example, by permitted remote entities.

The display unit 112 also may include controls to enable a user to enter information that controls, at least in part, aspects of the dialysis treatment, vertical (or lateral) movement of the ADM, solution bags, display unit or other components of the cart, movement of the cart itself via the wheel drive unit 124, or any suitable combination of the foregoing. These controls may be activated via keyboard, mouse, touchscreen input or the microphone 113.

The microphone 113 and one or more speakers 114 enable sound to be captured and projected, respectively, and may enable two-way communication between the smart cart 100 and a local user thereof, for example, a patient, caretaker or healthcare professional. The microphone 113 and the one or more speakers 114 may be configured to capture/project audio in relation to any of the information described in relation to the display unit 112, and may be controlled by the controller 108 or independently thereof, for example, by an ADM or remote device (e.g., of a permitted remote entity) coupled directly thereto. The control unit 108 and/or another component of the smart cart 100 may be configured to provide any of a variety or audio-related functions, including, for example: accepting voice commands (e.g., to adjust volume or make menu selections, etc.) from the local user captured by the microphone 113; playing voice automation of textual information being displayed on the display unit 112 on the one or more speakers 114; playing audio associated with video playing on the display unit 112; playing notifications and/or warnings over the one or more speakers 114; other functions; or any suitable combination of the foregoing.

The tactile user interface 116 may be configured to enable local users to interact with the smart cart 100. The tactile user interface 116 may include any of a variety of controls (e.g., buttons, switches) for controlling aspects of the dialysis treatment being performed, including any of the functions described herein, and may include braille writing symbols, or the like, on one or more the controls to assist users having visual impairment in using the tactile user interface 116. The tactile user interface 116 may include controls for controlling, at least in part, vertical (or lateral) movement of the ADM, solution bags, display unit or other components of the cart, and movement of the cart itself via the wheel drive unit 124.

The solution bag sensors 119 may be configured to detect the presence of, and information about, solution bags on the cart 100; e.g., solution bags supported by the solution bag supports 109. For example, the solution bag sensors may be equipped with one or more technologies (e.g., optical text recognition, bar code scanning; RFID sensing, other), by which any of a variety of information about the solution bag could be detected, including any of: type of solution, size of solution bag, expiration date, stock number, lot number, other information, or any suitable combination of the foregoing. The solution bag sensors 119 also may include one or more sensors (e.g., scales, strain gauges, heat sensors, liquid fill-level sensors (e.g., optical or sonic based)) for detecting one or more physical properties of the solution bags, including weight, solution fill level, proximate air temperature, etc. For example, the solution bag supports may include a spring-loaded member or the like on which solution bags rest, and from which weight can be determined. Further, one or more solution bag properties may be determined from other solution bag properties. For example, in addition to determining the solution fill level from a liquid fill-level sensor, the solution fill level may be determined by other means. For example, the height of the solution bag supports 109, initial weight and volume of the solution bag, and the unit weight of the solution may be known and predefined, e.g., in the control unit 108, from which the height of the solution in the solution bag may be determined based on a measured change in weight of the solution bag during a dialysis treatment.

The solution bag sensors 119 may be coupled to the control unit 108 and transmit the detected solution bag information thereto. The control unit 108 or one or more of the solution bag sensors 119 themselves may be configured to transmit the detected solution bag information to a coupled ADM and/or permitted remote entities. In some embodiments, detected solution bag information may be stored locally, e.g., in the solution bag sensors 119 and/or the control unit 108, and transmitted in batches to one or more permitted remote entities.

As described in more detail elsewhere herein, in some embodiments, information may be shared (i.e., communicated) in real-time between the smart cart 100 and the ADM to which it is coupled. In some embodiments, solution bag information, including solution bag information detected by the solution bag sensors 119 and by the ADM (if any) and solution bag information determined therefrom, may be shared between the smart cart 100 and the ADM. The smart cart 100 and/or ADM may be configured to analyze the shared solution bag information, determine whether to take action based on this analysis, and take action when it determines to do so. Such actions may include any of: communicating a message to the user (e.g., via the display unit 112 and/or one more speakers 114, or a display unit or speaker(s) of the ADM), communicating a message to permitted remote entities, altering the dialysis treatment, halting the treatment; other actions, or any suitable combination of the foregoing. For example, the smart cart 100 and/or the ADM may be configured to determine from the detected solution bag information whether the solution in each bag is the correct solution, e.g., within a sequence of solutions being administered to the patient as part of a dialysis treatment. If it is not the correct solution, a warning message may be communicated (visually and/or audially) to the user, for example, via the display unit 112 and/or one more speakers 114, a message may be communicated to permitted remote entities, and the treatment may be halted until the solution bag is replaced with a proper bag of solution and/or other desired or necessary steps are taken.

Including the one or more solution bag sensors 119 on the smart cart 100 as opposed to on an ADM may be desirable, as the smart cart 100 may provide more space within which to accommodate such sensors than an ADM, which may be smaller and have several other desirable features competing for space thereon.

The one or more drain bag sensors 120 may be configured to detect one or more physical properties of drain bags. One or more of the one or more drain bag sensors 120 may be disposed on the base 52 as illustrated in FIG. 1, and may include scales, strain gauges, heat sensors, etc., for detecting weight, proximate air temperature, and other physical properties of the solution bags. The smart cart 10 also may include one or more drain sensors (not shown) configured to detect one or more physical properties of the spent dialysis (i.e., dialysis effluent) that drains into the drain bag, for example, the fibrin content and cloudiness of the dialysis effluent. The one or more drain sensors may be disposed to detect these properties from the drain bag itself or may be disposed along a drain line between the patient and the drain bag.

In some embodiments, detected dialysis effluent and/or drain bag information may be shared between the smart cart 100 and a coupled ADM. The smart cart 100 and/or ADM may be configured to analyze the shared solution bag information, including effluent and/or drain bag information detected by the one or more drain sensors 123 and/or one or more drain bag sensors 120 and by the ADM (if any), determine whether to take action based on this analysis, and take action when it determines to do so. Such actions may include any of: communicating a message to the user (e.g., via the display unit 112 and/or one more speakers 114, or a display unit or speaker(s) of the ADM), communicating a message to permitted remote entities, altering the dialysis treatment, halting the treatment; other actions, or any suitable combination of the foregoing. For example, when abnormalities in fibrin content or cloudiness of the effluent are detected, the smart cart 100 and/or ADM may be configured to issue an audial and/or visual alert to a local user, send an alert communication to one or more permitted remoted parties, and halt or alter the dialysis treatment until desired or necessary steps are taken to resolve the abnormality.

ADMs may be configured to operate with disposable sets for automated dialysis treatment. For example, a set may include a disposable cassette and fluid lines (e.g., tubes) and other components. The cassette and ADM each may be configured such that the cassette is insertable into the ADM such that it is engaged therewith, the fluid lines are fed into the set, and the passing of the solution between the patient and the ADM through one or more of the patient lines, and the passing of fluid from patient to a drain bag, is under control of the ADM.

In some embodiments of the system described herein, the set sensor 118 of the smart cart 100 may be configured to detect the presence of, and information about, disposable dialysis sets ("sets") on the smart cart 100 and/or engaged with the ADM. For example, the set sensor 118 may be equipped with one or more technologies (e.g., optical text recognition, bar code scanning; RFID sensing, other), by which any of a variety of information about the set could be detected, including any of: type of set, number of solution bag connections, number of patient line connections, length of patient line(s), length of drain line(s), manufacturing date, expiration date, stock number, lot number, other information, or any suitable combination of the foregoing. The set sensor 118 may be coupled to the control unit 108 and transmit the detected set information thereto. The control unit 108 or the set sensor 118 itself may be configured to transmit the detected set information to a coupled ADM and/or permitted remote entities. In some embodiments, detected set information may be stored locally, e.g., in the set sensor 118 and/or the control unit 108, and transmitted in batches to one or more permitted remote entities.

In some embodiments, set information may be shared between the smart cart 100 and the ADM. The smart cart 100 and/or ADM may be configured to analyze the shared set information, including set information detected by the set sensors 121 and by the ADM (if any), determine whether to take action based on this analysis, and take action when it determines to do so. Such actions may include any of: communicating a message to the user (e.g., via the display unit 112 and/or one more speakers 114, or a display unit or speaker(s) of the ADM), communicating a message to permitted remote entities, altering the dialysis treatment, halting the treatment; other actions, or any suitable combination of the foregoing. For example, the smart cart 100 and/or ADM may be configured to update the displayed information on the display unit 112 to show only the number of fluid lines being used for connections to the ADM to minimize/reduce confusion. Further, any treatment algorithms embodied in software and/or hardware on the ADM and/or smart card may be configured (e.g., parameter values changed) based on the age of the set, the length of fluid lines, the number of patient line connectors, etc. to optimize the treatment.

Including the one or more set sensors 121 on the smart cart 100 as opposed to on an ADM may be desirable, as the smart cart 100 may provide more space within which to accommodate such sensors than an ADM, which may be smaller and have several other desirable features competing for space thereon.

The ADM sensor 117 may be configured to sense the presence of, and information about, an ADM on the smart cart 100, for example, using any of a variety or technologies, including RFID, infrared (IR), Bluetooth, NFC, bar coding scanning, the hall effect, etc. The information may include an identifier of the particular type, manufacturer and/or model of the ADM, and other information. The ADM sensor may be configured to communicate the detected information to the control unit 108 (or other component of the smart cart) configured to store (e.g., in a table) one or more sets of parameter values, where each set of parameter values corresponds to a particular type, manufacturer and/or model of ADM. The control unit may be configured to determine if it has a table entry corresponding to the detected ADM, and if so, to configure one or more smart cart parameters, programs and/or other logic according to the parameter values defined for the detected ADM, and to take other action based on these parameter values, including executing the programs or other logic. For example, a few of the parameters defined for an ADM may be the heights from its base to: a solution line connection and patient line connection, respectively. For example, the control unit 108 may be configured to control an initial height of solution bags and/or drain bags for dialysis treatment based on this ADM-specific information and other information, e.g., predefined properties of the smart cart (e.g., base and platform heights, solution bag support heights, entry point(s) of patient line(s) into the patient and egress point(s) of drain lines(s)), some of which may be predefined and/or learned from the ADM. Other examples of adjustments include raising or lowering platforms and/or other components on the smart cart 100, and perhaps lateral movements of components, to accommodate the geometry and/or use parameters of the ADM. Reciprocally, an ADM may be configured to sense the presence of the smart cart 100 and other information about the smart cart 100, including features that are available on the smart cart. The ADM may be configured to share control of the smart cart 100 based on this information as described in more detail elsewhere herein, including, for example, adjusting dialysis treatment algorithms and/or parameters thereof.

The control unit 108 may be configured to provide one or more control functions for the smart cart 100, and to this end may be configured to receive information from, and transmit information (including control signals) to, any of the components of the smart cart 100 described herein, and to transmit and/or receive information to/from a coupled ADM and permitted remote entities.

Figure 2:
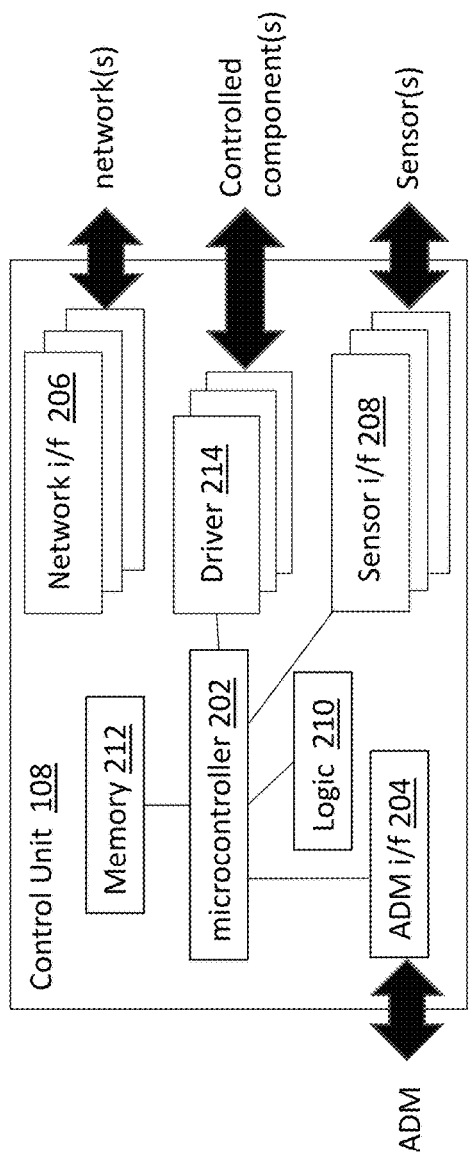
FIG. 2 is a block diagram illustrating an example of a control unit for a smart cart, according to embodiments of the system described herein.

FIG. 2 is a block diagram illustrating an example of a control unit 108 of a smart cart for an ADM, according to embodiments of the invention. Other embodiments of such a control unit, for example, variations of the control unit 108, are possible and are intended to fall within the scope of the system described herein. The control unit 108 may include any of: a microcontroller 202; an ADM interface 204; one or more network interfaces 206; one or more sensor interfaces 208; control logic 210; memory 212; one or more drivers 214; other components, or any suitable combination of the foregoing.

The microcontroller 202 may be the central control point (e.g., the "brains") of the control unit 108, and may include one or more CPUs, memory and I/O components that enable it to communicate with the other components of the control unit 108. The ADM interface 204 may provide a logical interface to an ADM coupled to the smart cart 100 and enable communications therebetween. The smart cart 100 may be coupled to an ADM by a physical electrical connection (e.g., a wire) or coupled wirelessly thereto, and the ADM interface may be configured to employ wireless and/or wire-based technologies accordingly, through which information (e.g., any of the information described herein) may be shared between the devices. In some embodiments of the system described herein, each of the smart cart 100 and a coupled ADM may be configured to share control of one or more functions implemented by each, including any of the functions described herein. For example, each device may be configured such that the ADM can display information and video and/or play sound (e.g., alarms, notifications, voice, video sound) on the display unit 112 and/or one or more speakers 114 of the smart cart 100 and/or raise or lower platforms of the smart cart 100, or components (e.g., solution bags) disposed on such platforms. The smart cart 100 and/or the ADM may be configured, individually or in a coordinated manner, to adjust automatically a height or lateral position of one or more platforms (e.g., the platform 56) or components thereof (solution bags) of the smart cart 100 to improve any of: patient access to smart cart controls or the ADM controls, patient visibility of information displayed on the smart card or the ADM; patient comfort; fluid fill and drain rates; sensor accuracy, other aspects of dialysis treatment, or any suitable combination of the foregoing. The information that may be used and shared between the smart cart 100 and coupled ADM to determine how to make these improvements include any of the information described herein, including: a height of the patient's bed, a distance of the patient's bed from the ADM; a length of patient lines and drain lines; a type, manufacturer and/or model of the ADM, a number of active patient lines and drains lines; height of a patient's head (e.g., estimated); a height of patient line connections and solution bag line connections on the ADM; height of drain line entry point (e.g., top of a catheter) into the patient's body; height of drain line egress point from the patient; solution bag and drain bag weights; room temperature, detected properties of the solution being passed to/from the patient and the effluent being drained from patient (e.g., fluid pressure, flow rate; cloudiness, temperature, chemical/biological composition, etc.); other information; or any suitable combination of the foregoing.

The one or more network interfaces 206 provide a logical interface to one or more networks (e.g., the Internet, mobile communication networks; other telephony networks, GPS networks, Bluetooth or Near Field Communications (NFC) networks); other networks and enable communications between such networks and the smart cart 100, thereby enabling communication between the smart cart 100 and permitted remote entities. The smart cart 100 may be connected by a hardline or wirelessly to the one or more networks, for example, via a gateway device, and the one or more network interfaces 206 may be configured accordingly with the appropriate wireless or wireline technologies. Each of the one or more sensor interfaces 208 may provide a logical interface between the control unit 108 and one or more sensors of the smart cart 100 described herein, thereby enabling communication between the control unit 108 and the sensors. The one or more drivers 214 provide a logical interface between the control unit 108 and one or more of the components described herein that may be controlled, e.g., in an automated fashion, by the control unit 108, enabling the control unit 108 to issue commands to the one or more components, as well as receive information therefrom.

The memory 212 may be used by the microcontroller 202, along with the memory of the microcontroller 202, to execute one or more programs or algorithms that implement any of the functions described herein. The programs or algorithms may be stored in the memory 212 itself, for example, in a non-volatile portion of the memory 212, and accessed by the microcontroller 202 for execution. In some embodiments, there are at least two discrete components of memory, a non-volatile memory for storing programs, program parameters and other information; and a volatile memory for use in executing programs, as described in more detail herein. In some embodiments, various functions or algorithms described herein, or portions thereof, may be implemented in the control logic 210, which may be hardware or firmware (e.g., ASICs, EPROM, EEPROM, programmable gateways, a printed circuit board, other hardware or firmware logic or any suitable combination of the foregoing), which may be executed independently or in conjunction with programs stored in the memory 212. Any of the information determined (including information received from the ADM or permitted remote entities) by the smart cart 100 may be stored in a non-volatile portion of the memory 212. This information may be stored in the memory 212 until it can be uploaded to another source, for example, a permitted remote entity, or until another event occurs (e.g., the memory is full) or a predefined amount of time has elapsed. The smart cart 100 also may include additional storage devices on which information can be stored, for example, under control of the control unit 108.

The various components of the control unit 108 may be configured to implement one or more of the functions described herein in relation to providing dialysis treatment, utilizing the various components of the smart cart 100 described herein.

Figure 3:
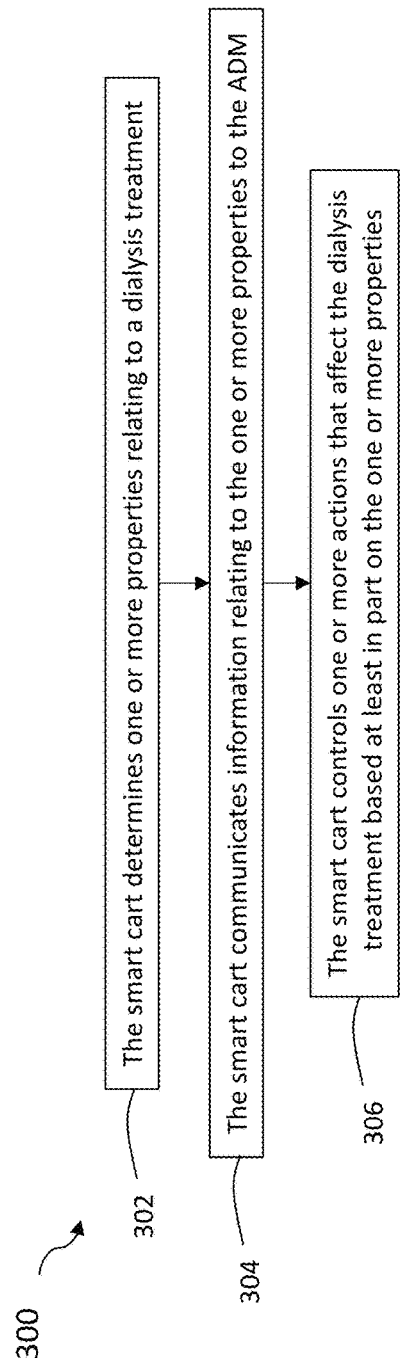
FIG. 3 is a flow chart illustrating an example of a method of using a smart cart to assist in providing dialysis treatment for patient, according to embodiments of the system described herein.

FIG. 3 is a flow chart illustrating an example of a method 300 of using a smart cart to assist in providing dialysis treatment for a patient, according to embodiments of the invention. Other embodiments of a method of using a smart cart to assist in providing dialysis treatment for a patient, for example, variations of the method 300, are possible and are intended to fall within the scope of the system described herein. The method 300, or portions thereof, may implemented or controlled using the smart cart 100 described in more detail herein, for example, at least in part as software, hardware and/or firmware of the control unit 108.

In a step 302, the smart cart may determine one or more properties relating to a dialysis treatment, for example, any of the properties described herein. These properties may be determined from information detected by sensors disposed on the smart cart itself, received from a coupled ADM or permitted remote entity or by other means. In a step 304, the smart cart may communicate information relating to the one or more properties to the ADM, for example, as described in more detail elsewhere herein. In a step 306, the smart cart may control one or more actions that affect the dialysis treatment based at least in part on the one or more properties, for example, as described in more detail elsewhere herein.

In some embodiments of the system described herein, the step 302 may include determining the relative heights of various elements of the smart cart 100, a coupled ADM, a sensor set of the coupled ADM and the patient location, including for example, a height of the a solution bag, a height of the solution bag line connection to the ADM, a height of the patient line connection to the ADM, and a height of the entry point of the patient line(s) (e.g., a top of a catheter) to/from the patient's body, for example, the abdomen (leading into the peritoneal cavity) in the case of peritoneal dialysis. In such embodiments, the step 302 also may include receiving information (from the ADM or an ancillary device) indicative of a measured pressure and/or flow rate of the solution in: the solution bag line (the line connecting the solution bag to the ADM), the patient line and/or the drain line; and the step 302 also may include determining information about the properties of the ADM itself, for example, based on the type, manufacturer or model of the ADM (from which some of the relative height information above may have been determined at least in part). In the step 304, the smart cart 100 may share some of this information with the ADM.

Continuing with the example, in the step 306, the smart cart 100, alone or in coordination with the ADM, may control an adjustment of height (and perhaps lateral position) of one or more platforms of the smart cart or components disposed thereon (e.g., solution bag supports 109) to attempt to maintain a certain fluid pressure and/or flow rate in the solution bag lines; patient lines(s) and/or drain lines (s). In some aspects of this embodiment, the step 306 may include attempting to maintain a constant relationship between a height of the solution in a solution bag and the entry point of the patient line into the patient and/or trying to achieve a maximum fill and/or drain rate (or maximum safe fill and/or drain rate); i.e., a maximum safe flow rate (or maximum safe flow rate) on the patient line from the ADM to the patient and on the drain line. In embodiments in which maximum safe flow rates are desired, these maximum values may be predefined within the control unit 108 (or elsewhere) on the smart cart 100, or in the ADM, and the fill rate and/or drain rate may be controlled (e.g., by adjustment of various heights as described above) to ensure the maximum safe rates are not exceeded.

It should be appreciated that the height of patient's head during dialysis treatment (the patient is often reclined in bed, and hopefully sleeping, during automated dialysis) impacts the pressures and flow rates on the patient lines and drain lines. In some embodiments of the invention, the smart cart is configured to raise the height of the ADM patient lines as high as possible relative to the head height to create the maximum flow rates and/or fluid pressure in the patient and drain lines. The head height may be estimated from other predefined or determined properties, for example, bed height of the entry point into the body of the patient line.

Maximizing the fill rate and drain rate during a dialysis cycle reduces the time it takes to fill and drain a patient, during which time the patient is partially filled, and thus increases the dwell time of the solution within the patient during a dialysis cycle, thereby improving the dialysis treatment.

Implementations discussed herein may be combined with each other in appropriate combinations in connection with the system described herein. Additionally, in some instances, the order of steps in the flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions. Data exchange and/or signal transmissions to, from and between components of the system may be performed using wired or wireless communication. This communication may include use of one or more transmitter or receiver components that securely exchange information via a network, such as the Internet, and may include use of components of local area networks (LANs) or other smaller scale networks, such as WiFi, Bluetooth or networks using other short-range transmission protocols, and/or components of wide area networks (WANs) or other larger scale networks, such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a memory card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c].

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A support assembly for a dialysis machine, comprising:
   one or more substantially planar platforms, at least a first of the one or more substantially planar platforms supporting the dialysis machine;
   a control unit that determines one or more properties relating to a dialysis treatment being performed on a patient using the dialysis machine, communicates information relating to the one or more properties to the dialysis machine, and controls one or more actions that affect the dialysis treatment based at least in part on the one or more properties, wherein the control unit is part of the support assembly, which is separate from and communicatively coupled to the dialysis machine;
   three or more wheels that provide horizontal movement of the support assembly;
   a powered motor coupled to at least one of the at least three wheels to provide powered movement of the cart; and
   a member that measures a weight of a solution bag before and during the dialysis treatment,
   wherein the control unit determines a height of a solution in the solution bag based at least in part on the measured weight.

2. The support assembly of claim 1, wherein the control unit includes platform control logic that controls a height of the first platform based on at least one of the one or more properties.

3. The support assembly of claim 2, wherein the at least one property includes: a height of the dialysis machine and a height of the patient.

4. The support assembly of claim 1, further comprising:
   a display screen that displays information associated with dialysis treatment provided by the dialysis machine.

5. The support assembly of claim 1, further comprising:
   one or more support members for supporting a bag of solution coupled to the dialysis machine that supplies the solution introduced into the patient during the dialysis treatment, and
   a liquid fill-level sensor that detects a height of solution in the bag as the solution is emptied from the bag into the patient during the dialysis treatment, wherein the height of the solution is one of the one or more properties and wherein the one or more actions include adjusting a height of the bag based on the height of the solution in the bag to attempt to maintain a constant height of the solution relative to an entry point of the solution into the patient during the dialysis treatment.

6. The support assembly of claim 1, wherein the control unit includes a memory storing parameter values corresponding to one or more types of dialysis machines, wherein the support assembly includes a dialysis machine sensor that detects a type of the dialysis machine, wherein the one or more properties includes the detected type of the dialysis machine, wherein the control unit controls the one or more actions based at least in part on the detected type of the dialysis machine.

7. The support assembly of claim 1, further comprising:
   a user interface that receives manual input from a user, wherein the control unit controls the one or more actions based at least in part on the manual input from the user.

8. The support assembly of claim 1, wherein at least one of the properties indicates a location of the patient, the support assembly further comprising:
   a steering control unit coupled to at least one of the three wheels that controls the at least one wheel to turn laterally; and
   a position control unit coupled to the steering control mechanism and the powered motor that receives the at least one property indicating the location of the patient, detects a change in location of the patient, and controls the steering control unit and the powered motor to cause movement of the support assembly in response to the detected change.

9. The A method of providing dialysis treatment on a patient, comprising:
   providing a support assembly for a dialysis machine that determines one or more properties relating to the dialysis treatment being performed using the dialysis machine;
   communicating, using the support assembly, information relating to the one or more properties to the dialysis machine, wherein the communicating is controlled by a control unit that is part of the support assembly, which is separate from and communicatively coupled to the dialysis machine;

controlling, using the support assembly, one or more actions that affect the dialysis treatment based at least in part on the one or more properties, wherein the support assembly includes three or more wheels that provide horizontal movement of the support assembly, and a powered motor coupled to at least one of the at least three wheels to provide powered movement of the cart, and wherein controlling the motor controls movement of the cart;

measuring a weight of a solution bag before and during the dialysis treatment; and the control unit determining a height of a solution in the solution bag based at least in part on the measured weight.

10. The method of claim 9, wherein controlling one or more actions includes controlling a height of a platform that supports the dialysis machine based on at least one of the one or more properties.

11. The method of claim 9, wherein the at least one property includes: a height of the dialysis machine and a height of the patient.

12. The method of claim 9, wherein the support assembly includes a display screen, and the method further comprises:
displaying information associated with the dialysis treatment on the display screen.

13. The method of claim 9, wherein the support assembly includes one or more support members for supporting a bag of solution coupled to the dialysis machine that supplies the solution introduced into the patient during the dialysis treatment, wherein determining one or more properties includes detecting a height of solution in the bag as the solution is emptied from the bag into the patient during the dialysis treatment, and wherein controlling the one or more actions includes adjusting a height of the bag based on the height of the solution in the bag to attempt to maintain a constant height of the solution relative to an entry point of the solution into the patient during the dialysis treatment.

14. The method of claim 9, wherein the support assembly includes a memory storing parameter values corresponding to one or more types of dialysis machines,
wherein determining one or more properties includes detecting a type of the dialysis machine, and
wherein the one or more actions are controlled based at least in part on the detected type of the dialysis machine.

15. The method of claim 9, wherein the support assembly includes a user interface, wherein the method further comprises receiving manual input from a user through the user interface, and wherein the one or more actions are controlled based at least in part on the manual input from the user.

16. The method of claim 9, wherein the support assembly includes a steering control unit coupled to at least one of the three wheels that controls the at least one wheel to turn laterally,
wherein determining one or more properties includes determining a location of the patient and detecting a change in location of the patient, and
wherein controlling one or more actions includes controlling the steering control unit and the powered motor to cause movement of the support assembly in response to the detected change.

17. A non-transitory computer-readable medium having software stored thereon for providing dialysis treatment on a patient using a support assembly on which a dialysis machine is supported, the software comprising:
executable code that uses the support assembly to determine one or more properties relating to the dialysis treatment being performed using the dialysis machine;
executable code that controls communication of information relating to the one or more properties from the support assembly to the dialysis machine;
executable code that uses the support assembly to control one or more actions that affect the dialysis treatment based at least in part on the one or more properties, wherein the support assembly includes three or more wheels that provide horizontal movement of the support assembly and a powered motor coupled to at least one of the at least three wheels to provide powered movement of the cart and wherein controlling the motor controls movement of the cart;
executable code that controls measuring a weight of a solution bag before and during the dialysis treatment; and
executable code that determines a height of a solution in the solution bag based at least in part on the measured weight,
wherein the non-transitory computer-readable medium is included in a control unit that is part of the support assembly, which is separate from and communicatively coupled to the dialysis machine.

18. The non-transitory computer-readable medium of claim 17, wherein the support assembly includes one or more support members for supporting a bag of solution coupled to the dialysis machine that supplies the solution introduced into the patient during the dialysis treatment, and a liquid fill-level sensor that detects a height of solution in the bag as the solution is emptied from the bag into the patient during the dialysis treatment, and
wherein the software further comprises executable code that controls adjusting a height of the bag based on the height of the fluid in the bag to attempt to maintain a constant height of the fluid relative to an entry point of the solution into the patient during the dialysis treatment.

* * * * *